(12) United States Patent
Raksi

(10) Patent No.: US 10,383,767 B2
(45) Date of Patent: Aug. 20, 2019

(54) OPHTHALMIC RELAXING INCISIONS AND ASSOCIATED DEVICES, SYSTEMS, AND METHODS

(71) Applicant: Novartis AG, Basel (CH)

(72) Inventor: Ferenc Raksi, Mission Viejo, CA (US)

(73) Assignee: Novartis AG (CH)

( * ) Notice: Subject to any disclaimer, the term of this patent is extended or adjusted under 35 U.S.C. 154(b) by 401 days.

(21) Appl. No.: 14/973,117

(22) Filed: Dec. 17, 2015

(65) Prior Publication Data

US 2017/0172801 A1 Jun. 22, 2017

(51) Int. Cl.
*A61F 9/008* (2006.01)
(52) U.S. Cl.
CPC ...... *A61F 9/00804* (2013.01); *A61F 9/00827* (2013.01); *A61F 2009/00872* (2013.01); *A61F 2009/00897* (2013.01)
(58) Field of Classification Search
CPC .............. A61F 9/00827; A61F 9/00804; A61F 2009/00897; A61F 2009/00872
See application file for complete search history.

(56) References Cited

U.S. PATENT DOCUMENTS

| | | | |
|---|---|---|---|
| 5,549,632 A * | 8/1996 | Lai | A61F 9/00825 606/10 |
| 6,325,792 B1 | 12/2001 | Swinger et al. | |
| 8,506,559 B2 | 8/2013 | Raksi | |
| 2008/0312675 A1 | 12/2008 | Newcott et al. | |
| 2009/0137988 A1 | 5/2009 | Kurtz | |
| 2010/0324542 A1 | 12/2010 | Kurtz | |
| 2011/0022037 A1 | 1/2011 | Bille et al. | |
| 2011/0028957 A1 | 2/2011 | Raksi et al. | |
| 2011/0040293 A1 | 2/2011 | Bor | |
| 2012/0296321 A1 * | 11/2012 | Frey | A61F 9/00827 606/5 |
| 2013/0165911 A1 | 6/2013 | Raksi et al. | |
| 2016/0213513 A1 | 7/2016 | Nevyas-Wallace | |

* cited by examiner

*Primary Examiner* — Scott Luan
(74) *Attorney, Agent, or Firm* — Keiko Ichiye, Esq.

(57) ABSTRACT

A surgical laser system can include a laser source configured to generate a laser beam. The system can also include a scanning delivery system that can be configured to direct the laser beam to an ocular target region and scan the laser beam along a scan pattern in the ocular target region of an eye. The system can further include a system controller in communication with the scanning delivery system. The system controller can be configured to control the scanning delivery system to scan the laser beam along the scan pattern to create a pattern of cuts for relaxing ophthalmic tissue in the ocular target region. Each cut of the pattern of cuts can extend only partially through the ophthalmic tissue.

19 Claims, 10 Drawing Sheets

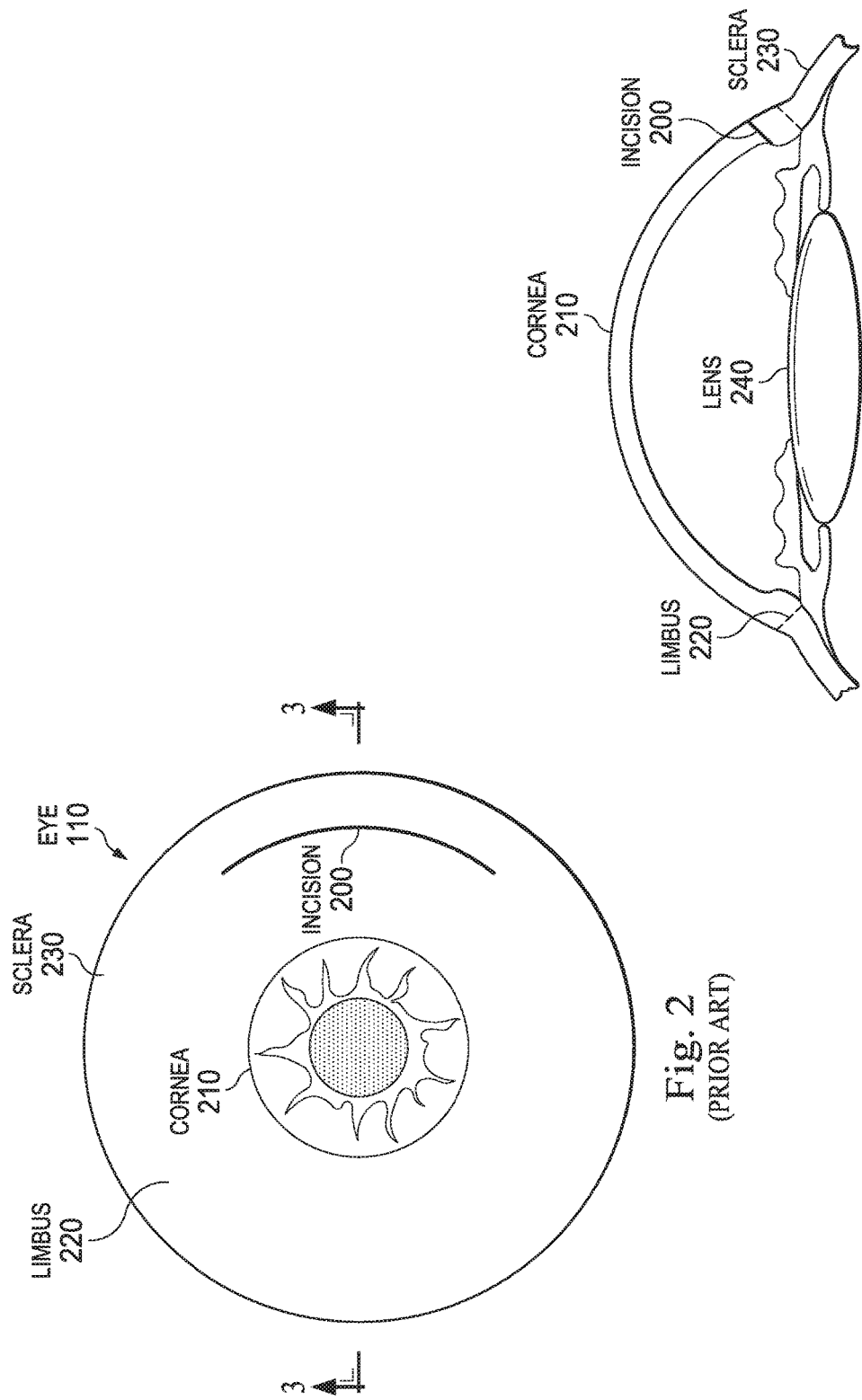

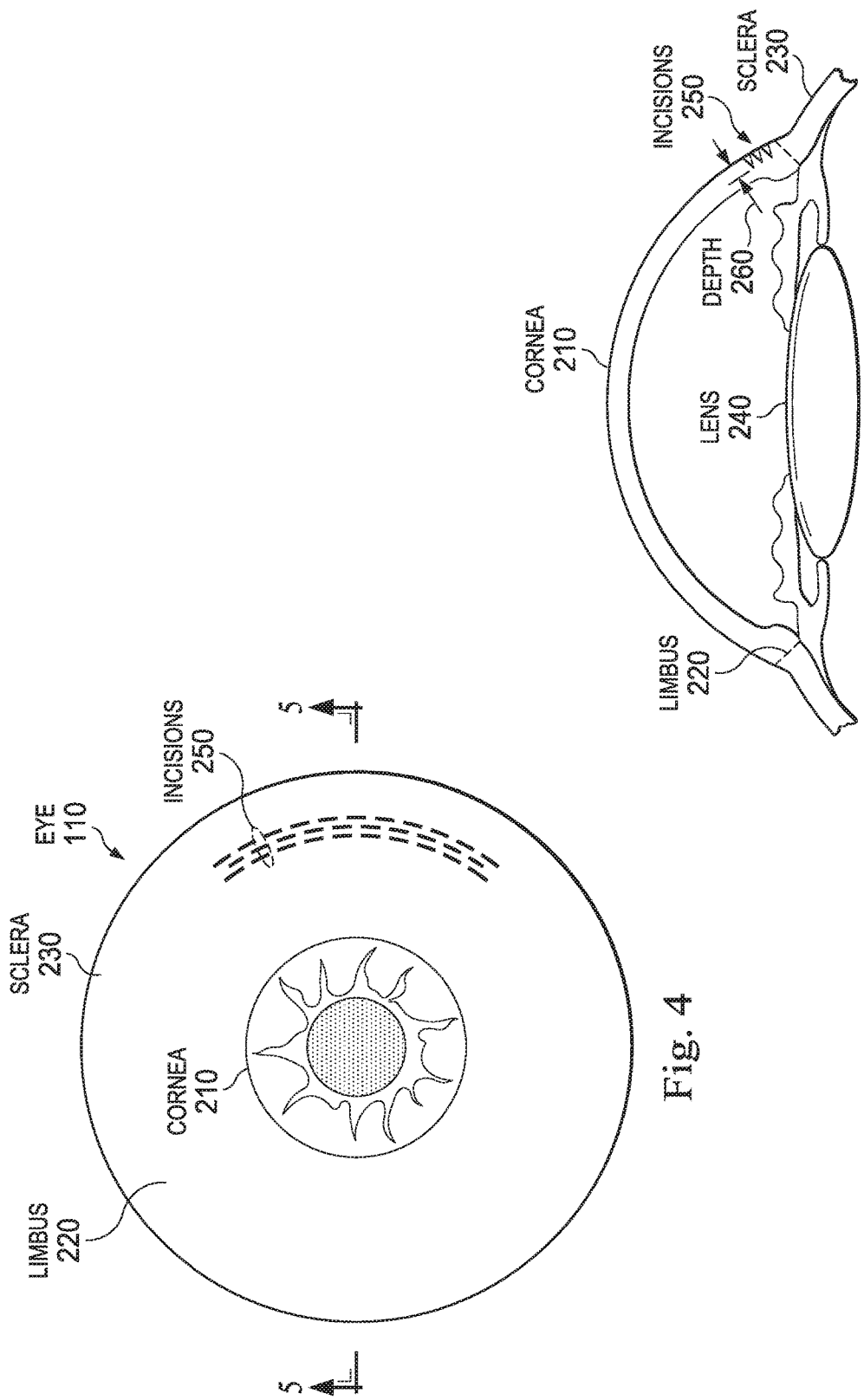

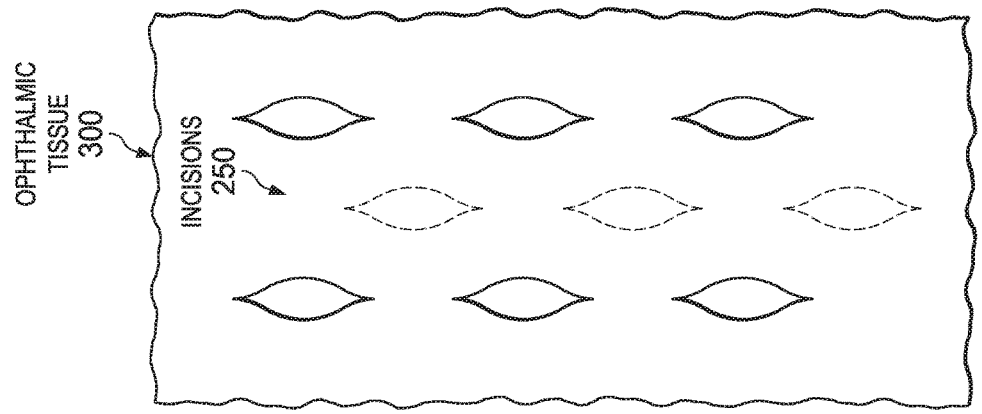
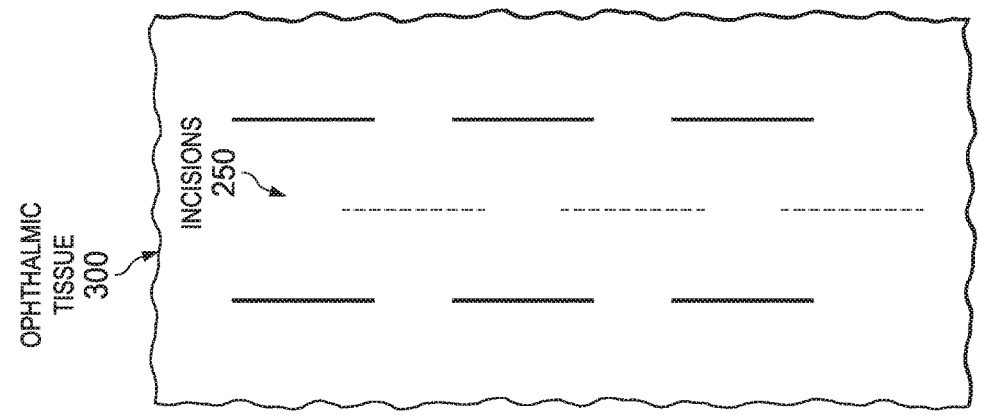

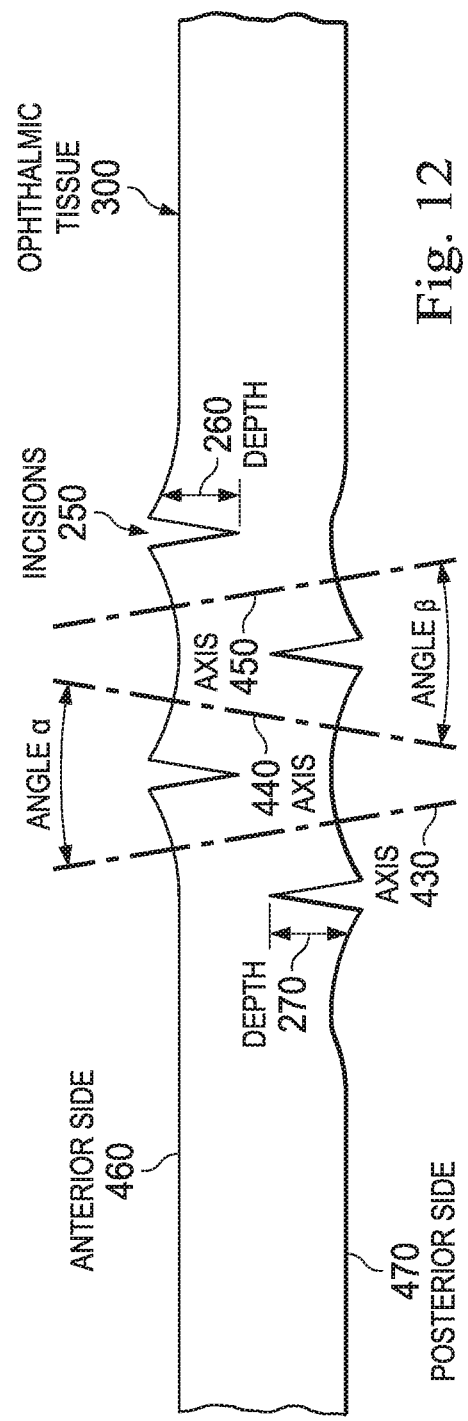

OPHTHALMIC RELAXING INCISIONS AND ASSOCIATED DEVICES, SYSTEMS, AND METHODS

BACKGROUND

Technical Field

Embodiments disclosed herein can relate to methods and systems for performing eye surgery. More specifically, embodiments described herein can relate to making incisions in a patient's eye to correct vision problems.

Related Art

Ophthalmic microsurgical procedures can require precision cutting and/or removing of various tissues of the patient's eye. Some of these procedures can be undertaken to correct corneal astigmatisms, defined as cylindrical abnormalities of the curvature of the cornea. These procedures typically include making incisions, known as Limbal Relaxing Incisions (LRI) and Astigmatic Keratotomy (AK), in the limbus and cornea of the eye, collectively called arcuate incisions. When placed correctly, these cuts can relax tissue in the limbus and cornea thereby helping to correct corneal curvature. LRI procedures typically use long, arcuate incisions that penetrate through 80% to 90% of the depth of the ophthalmic tissue in the limbus and cornea region of the eye. These procedures can require a high level of precision in the placement of incisions and may only correct a small range of astigmatic aberrations.

Accordingly, there remains a need for improved devices, systems, and methods that allow more precise ophthalmic surgeries and correction of a larger range of astigmatic aberrations while maintaining the strength and integrity of the ophthalmic tissue.

SUMMARY

The presented solution fills an unmet medical need with a unique solution of making patterns of incisions in ophthalmic tissue that extend only partially through tissue layers. The patterns can include incisions spaced apart and aligned along line segments and arcs. Additionally, the patterns can originate on both the anterior and posterior sides of the ophthalmic tissue. These incision patterns can provide greater elasticity of the ophthalmic tissue, as well as more precise shaping, while maintaining the overall strength and integrity of the ophthalmic tissue.

Consistent with some embodiments, an ophthalmic surgical laser system can be provided. The ophthalmic surgical laser system can include a laser source. The laser source can be configured to generate a laser beam. The ophthalmic surgical laser system can also include a scanning delivery system. The scanning deliver system can be configured to direct the laser beam to an ocular target region and scan the laser beam along a scan pattern in the ocular target region of an eye. The ophthalmic surgical laser system can also include a system controller in communication with the scanning delivery system. The system controller can be configured to control the scanning delivery system to scan the laser beam along the scan pattern to create a pattern of cuts for relaxing ophthalmic tissue in the ocular target region. Each cut of the pattern of cuts can extend only partially through the ophthalmic tissue.

Consistent with some embodiments, a method of performing an ophthalmic surgical procedure can be provided. The method can include the steps of generating a laser beam with a laser source, directing the laser beam to an ocular target region, and scanning the laser beam along a scan pattern within the ocular target region to create a pattern of cuts for relaxing ophthalmic tissue in the ocular target region. Each cut of the pattern of cuts can extend only partially through the ophthalmic tissue.

Additional aspects, features, and advantages of the present disclosure will become apparent from the following detailed description.

BRIEF DESCRIPTION OF THE DRAWINGS

FIG. 2 illustrates a front view of an eye of a patient showing a prior art limbal relaxing incision.

FIG. 3 illustrates a cross-sectional side view of the eye of FIG. 2 taken along the section line 3-3.

FIG. 4 illustrates a front view of an eye of a patient showing a set of incisions.

FIG. 5 illustrates a cross-sectional side view of the eye of FIG. 4 taken along the section line 5-5.

FIG. 10 illustrates a region of relaxed ophthalmic tissue showing a set of incisions.

FIG. 11 illustrates the region of ophthalmic tissue of FIG. 10 under stress.

FIG. 12 illustrates a cross-sectional side view of a region of stressed ophthalmic tissue with incisions on the anterior and posterior sides.

Figure 1:
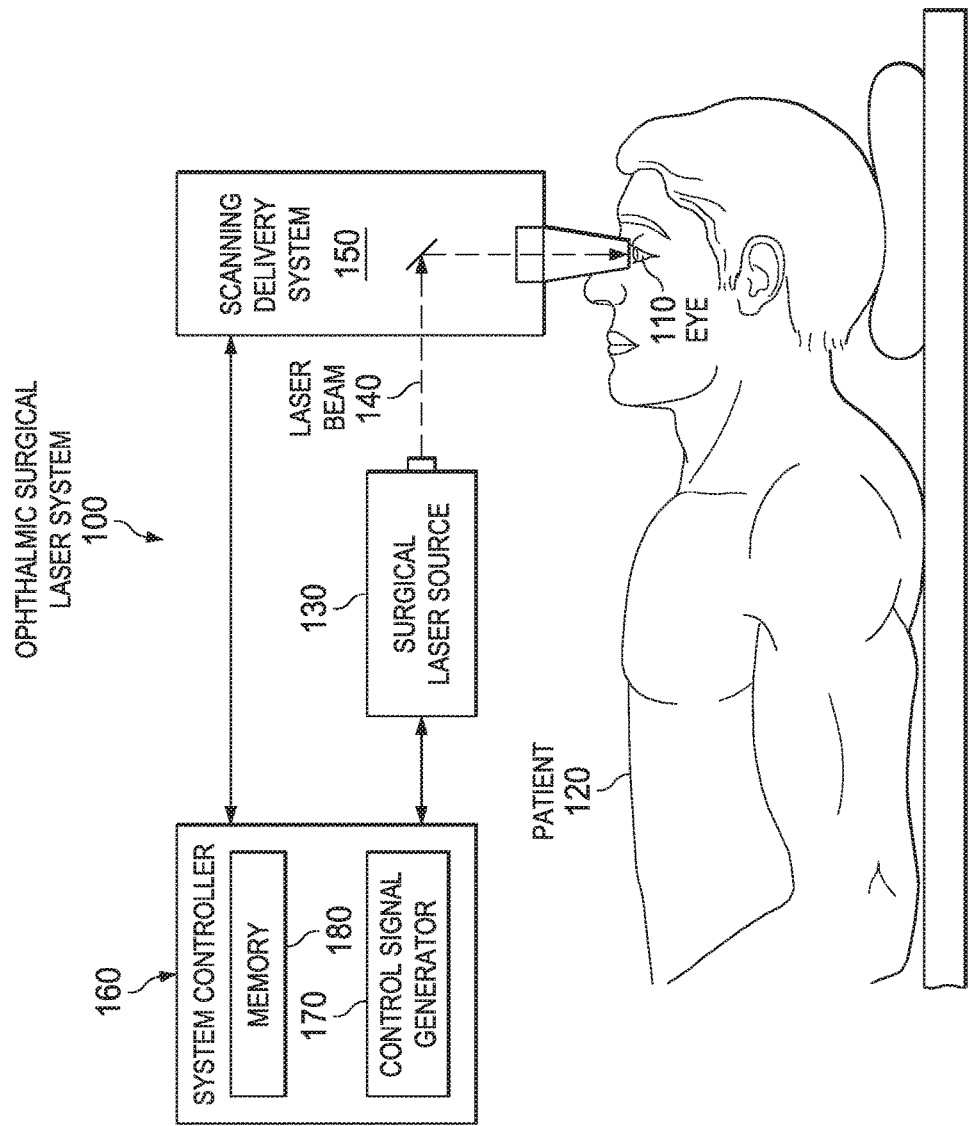
FIG. 1 illustrates a schematic diagram of an ophthalmic surgical laser system.

In the drawings, elements having the same designation have the same or similar functions.

DETAILED DESCRIPTION

In the following description, specific details can be set forth describing certain embodiments. It will be apparent, however, to one skilled in the art that the disclosed embodiments may be practiced without some or all of these specific details. Specific and/or illustrative, but not limiting, embodiments can be presented herein. One skilled in the art will realize that other material, although not specifically described herein, can be within the scope and spirit of this disclosure.

The present disclosure describes devices, systems, and methods of making incisions into ophthalmic tissue in order to mechanically deform the tissue or to change its elastic properties thereby changing the shape of the eye and its refractive properties. For example, incisions in the sclera, cornea, or limbus of a patient's eye can allow the ophthalmic tissue to stretch to facilitate changes in the curvature of the cornea. Moreover, incisions of different shapes or depths can shape ophthalmic tissue in numerous ways. Some types of incisions can increase the range of stretching of ophthalmic tissue without compromising its strength. Aberrations in the shape of the eye, such as astigmatisms, can be corrected using the incision or set of incisions.

The devices, systems, and methods of the present disclosure provide numerous advantages. For example:

(1) The present disclosure can require smaller cutting depth into ophthalmic tissue to achieve a desired shape. Existing methods of bisecting ophthalmic tissue 80% to 90% or more can cause damage to underlying tissue, increase the chance of infection, and cause incision dehiscence on the ophthalmic tissue. The set of incisions of the present disclosure can be applied at shallower depths in the ophthalmic tissue to correct astigmatisms. A pattern of incisions that partially cuts through the tissue can be sufficient to correct a wide range of astigmatic aberrations.

(2) The present disclosure can allow greater strength retention of ophthalmic tissue. In particular, incision patterns can include uncut ophthalmic tissue disposed around incisions. This uncut tissue can lend strength and integrity to the overall operative tissue region. Cutting only partially at shallower depths through ophthalmic tissue layers can also facilitate increased strength and integrity for the ophthalmic tissue.

(3) More extensive astigmatic aberrations can be treated with the present disclosure than previous methods. In particular, sets of incisions can be designed to relax large areas of ophthalmic tissue without compromising tissue strength. Sets of incisions can also include incisions in different regions of the eye, allowing greater correction of corneal astigmatisms.

(4) The present disclosure can yield corrective results while requiring less precision in performing a biometry. Existing methods can rely on exact measurements of the thickness of the cornea along the incision site before cutting. Miscalculations can lead to ineffective procedures and injury to underlying ophthalmic tissue. The present disclosure can allow a larger margin of error in corneal calculations by allowing increased relaxation of ophthalmic tissue with a less invasive procedure.

(5) The present disclosure can yield corrective results while requiring less precision in performing eye surgery. In particular, existing methods can rely on exact placement of the incision as well as exact incision length to achieve desired results. Procedures to correct erroneous incisions can be complicated and can carry additional health risks. The present disclosure can allow a larger margin of error in the placement of incisions. In particular, the aggregate effect of a set of incisions can be effectively fine-tuned by varying the shape, number, depth, and placement of a number of small incisions.

(6) The present disclosure can yield more predictable refractive outcomes. In particular, the present disclosure can allow for a more precise surgical procedure by allowing more complete customization of the incision pattern to the curvature of a particular cornea. Various incisions patterns can also be used to address larger astigmatic aberrations. Furthermore, the present disclosure can allow greater tolerance to variations in the execution of the surgical procedure.

FIG. 1 illustrates an ophthalmic surgical laser system 100. The ophthalmic surgical laser system 100 can include a surgical laser source 130 configured to generate a laser beam 140. The ophthalmic surgical laser system 100 can also include a scanning delivery system 150 configured to direct the laser beam 140 to an ocular target region on an eye 110 of a patient 120. Furthermore, the scanning delivery system 150 can be configured to scan the laser beam 140 along a scan pattern in the ocular target region of the eye 110.

The ophthalmic surgical laser system 100 can also include a system controller 160. The system controller 160 can be configured to control the scanning delivery system 150 to scan the laser beam 140 along a scan pattern to create a pattern of cuts or incisions 250 for relaxing ophthalmic tissue 300 in the ocular target region. Some of the patterns include incisions 250 that extend partially through the ophthalmic tissue 300. The incisions 250 can have many different depths, angles, and orientations. FIGS. 4-19 can illustrate exemplary incisions 250.

The system controller 160 can comprise a memory 180 and a control signal generator 170. The memory 180 can be configured to store an instruction set for controlling the scanning delivery system 150. In some cases, the control signal generator 170 can be configured to output control signals to the scanning delivery system 150 corresponding to the stored instruction set. In particular, the control signals can instruct the scanning delivery system 150 to scan the laser beam 140 along the scan pattern.

FIG. 2 illustrates a front view of the eye 110 of the patient 120 according to prior art optical procedures. Regions of the eye 110 relevant for purposes of the present disclosure can include a cornea 210, limbus 220, sclera 230, lens 240, and/or other suitable anatomy of the eye 110. Generally, existing limbal relaxing and astigmatic keratotomy procedures can involve a single arcuate incision 200 in the limbus 220 of the eye 110 or a pair of laterally opposing incisions.

As can be seen in FIG. 3, the incision 200 in existing procedures can pass nearly entirely through the layer of ophthalmic tissue 300. However, such an incision 200 can require highly precise measurements to correctly place the incision 200 in the ophthalmic tissue 300, correctly ascertain the thickness of the tissue 300 at the site of the incision 200, and predict the refractive outcome of the incision 200. Furthermore, the amount of refractive correction possible can be very limited by use of a single incision 200. Also, the integrity of the ophthalmic tissue 300 can be compromised due to the incision 200 passing so deeply into the ophthalmic tissue 300, which can lead to undesirable results.

FIG. 4 illustrates an example of the present disclosure as seen on a front view of the eye 110. In this case, a set of incisions 250 forming one or more line segments or arcs can be made on ophthalmic tissue 300 on the cornea 210 or limbus 220. However, the present disclosure contemplates making incisions 250 in the sclera 230 and the cornea 210 of the eye, as well as in other layers of ophthalmic tissue 300 including the lens 240 and connective tissue. This set of incisions 250 can take the form of a set of parallel lines, a cut mesh, a cut grating, or a pattern of staggered cuts 250. The set of incisions 250 can include one, two, three, four, or more individual incisions.

The incisions 250 can form arcs that extend concentrically around the cornea 210, as seen in FIG. 4. In particular, each of the one or more arcs can be defined by multiple incisions 250 spaced apart from one another with uncut ophthalmic tissue remaining around each incision 250. The arcs can be staggered or inter-digitated relative to one another. In particular, incisions 250 of one arc can be at least partially aligned with incisions 250 of another arc. A ray originating from a center of the cornea 210 can pass through incisions 250 of both arcs. Sufficient space can be placed between incisions 250 so that a line segment can be traced over uncut ophthalmic tissue lying between the outer boundaries of the pattern of incisions 250.

One or more of the incisions 250 can extend at a different radius, angle, depth, length, spacing, etc., relative the cornea 210 than other incisions 250. The incisions 250 can also extend into the ophthalmic tissue 300 at various angles besides vertically. For example, the incisions 250 can extend perpendicular to the anterior side 460 of ophthalmic tissue 300. Incisions 250 can also be made at various angular measurements from normal. In some cases, the incisions 250 can be made at between approximately 10 degrees and approximately 20 degrees from normal, between approximately 20 degrees and approximately 45 degrees from normal, between approximately 45 degrees and approximately 80 degrees from normal, and/or other suitable values both larger and smaller. Additionally, a pattern of incisions can include individual incisions 250 that enter the ophthalmic tissue 300 at different angles. In any case, the particular parameters of the incisions 250 can be selected based on the desired astigmatism correction.

FIG. 5 illustrates a cross-sectional side view of the eye 110 of the patient 120, showing the incisions 250 that can be made in the cornea 210, limbus 220, or sclera 230 of the eye 110. The incisions 250 can extend partially through the ophthalmic tissue 300. Generally, the thickness of the ophthalmic tissue 300 in or near the cornea 210 can be about 600 μm. The depth 260 of the incisions 250 can measure between 10% and 80% of the tissue thickness, between 20% and 75% of the thickness, between 30% and 70% of the thickness, between 40% and 60% of the thickness, and/or other suitable values both larger and smaller. In some cases, these percentages can correspond to approximately 60 μm to 480 μm, 120 μm to 450 μm, 180 μm to 420 μm, and 240 μm to 360 μm, respectively, and/or other suitable values both larger and smaller. Advantageously, the depth 260 of the incisions 250 can be less than in prior art methods. The depth 260 chosen for the incisions 250 can impact both the change in shape to the cornea 210 as well as the strength of the ocular target region of ophthalmic tissue 300.

Figure 6:
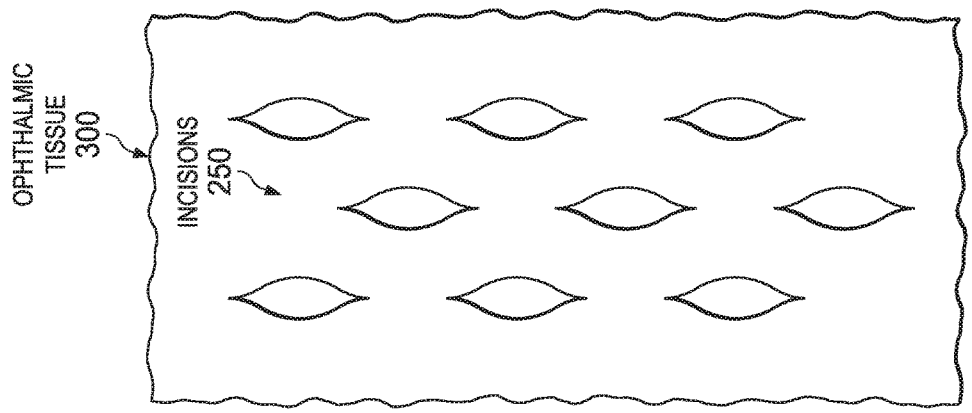
FIG. 6 illustrates a region of relaxed ophthalmic tissue showing a set of incisions.
Figure 7:
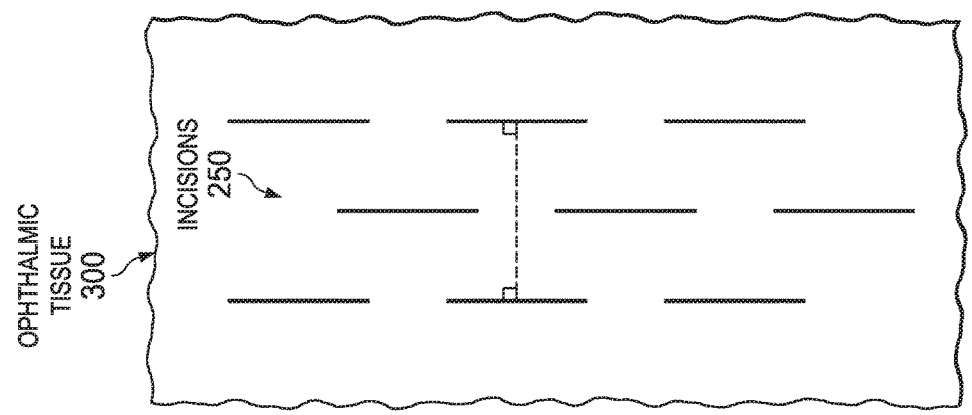
FIG. 7 illustrates the region of ophthalmic tissue of FIG. 6 under stress.

FIGS. 6 and 7 illustrate a region of ophthalmic tissue 300. FIG. 6 shows a region of relaxed ophthalmic tissue 300 with several incisions 250. The incisions 250 themselves can have any suitable cross-sectional shape, including a straight line segment as shown, arcuate line segment, polygon, ellipse, other suitable shape(s), and/or combination(s) thereof. In some cases, an incision 250 can be disposed parallel to one or more other incisions 250. For example, two incisions 250 are disposed parallel to each other in FIG. 6. As shown, the two incisions 250 can both be perpendicular to a transverse line between them, which indicates that they are parallel to one another. Different subsets of the incisions 250 can be disposed along axes parallel to one another. For example, the three incisions 250 on the left in FIG. 6 can be parallel to the three incisions 250 in the middle and the three incisions on the right.

The incisions 250 can form one or more line segments or arcs that contain multiple incisions 250. The line segments or arcs can be equally spaced from one another or separated by differing distances. The line segments or arcs can be parallel relative to one another in some instances. The incisions 250 forming the line segments or arcs can be bounded by uncut ophthalmic tissue 300. In particular, the incisions 250 can create a mesh structure of uncut ophthalmic tissue. Such a mesh structure can lend strength to the ophthalmic tissue 300 in the target area while allowing for large variations in the shape of the cornea 210. The boundaries of the mesh structure can be the central portion of the ocular target region and a peripheral portion of the ocular target region (e.g., defined as the side boundaries of FIG. 6), as well as the two outer boundaries of the incision pattern (e.g., defined by the upper and lower boundaries of FIG. 6). In the example of FIG. 6, the incisions 250 can be staggered and/or deep enough such that a horizontal line passing through the ophthalmic tissue 300 would pass through more than one incision 250.

FIG. 7 shows a region of ophthalmic tissue 300 with incisions 250 under strain. This strain can be caused by the internal pressure of the eye 110 and can be compounded by external sources of pressure. The mesh structure of uncut ophthalmic tissue can be seen in this example as the connecting tissue around incisions 250.

The incisions 250 can modify an elastic property of the ophthalmic tissue 300. In the example of FIG. 7, vertical incisions 250 can be placed in a tangential configuration with respect to the cornea 210. In particular, the elastic property of the ophthalmic tissue 300 in the tangential direction (vertical in this case) can be modified to a different degree than the elastic property of the ophthalmic tissue 300 in the radial direction (horizontal in this case).

In the example of FIG. 7, the elasticity of the ophthalmic tissue 300 can be made greater by the incisions 250 in the radial direction than in the tangential direction. The elasticity in the radial direction can be increased more than the elasticity in the tangential direction by a factor of 1.5:1 or greater, 2:1 or greater, 3:1 or greater, and/or other suitable values both larger and smaller. Conversely, placing the incisions 250 in a radial configuration with respect to the cornea 210 can allow more elasticity of ophthalmic tissue 300 in the tangential direction as compared to elasticity in the radial direction.

Figure 9:
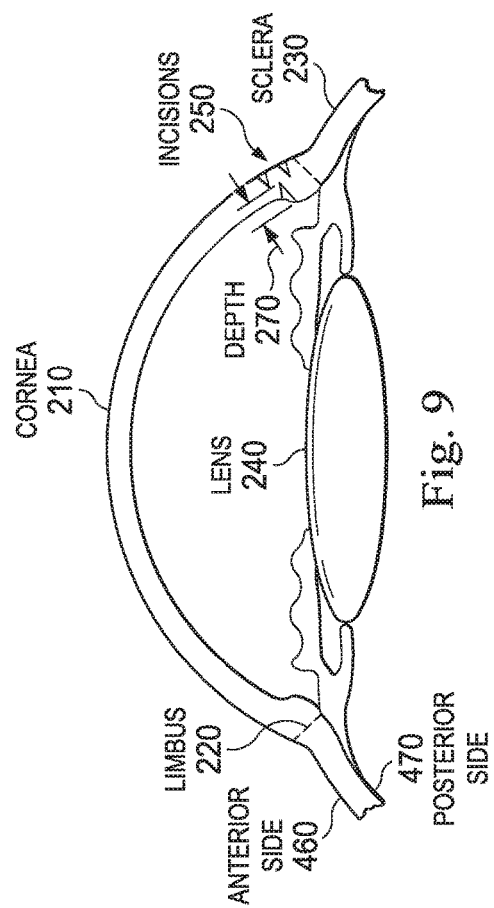
FIG. 9 illustrates a cross-sectional side view of the eye of FIG. 8 taken along the section line 9-9.
Figure 8:
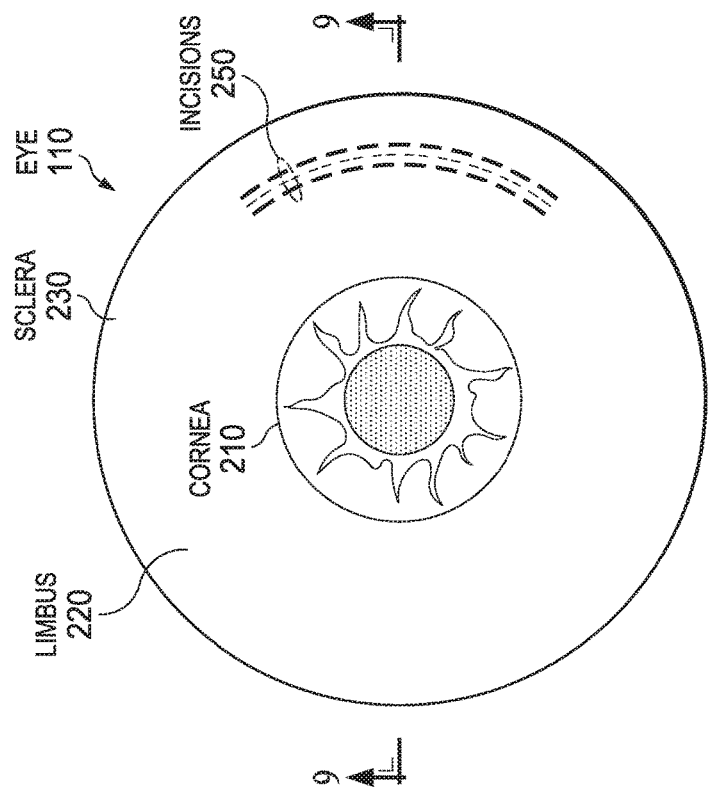
FIG. 8 illustrates a front view of an eye of a patient showing a set of incisions.

FIGS. 8 and 9 illustrate incisions 250 made on both an anterior side 460 and a posterior side 470 of the eye 110. The anterior side 460 and the posterior side 470 can be seen in more detail in connection with FIG. 12. The laser system 100 of the present disclosure can be configured to cut ophthalmic tissue 300 at various depths 260, 270. Furthermore, one or more incisions 250 can have an origin at the posterior side 470 of ophthalmic tissue 300. These incisions 250 can be configured to extend out from the posterior side 470 to the depth 270.

In some cases, incisions 250 can originate from both the anterior side 460 and posterior side 470 of ophthalmic tissue 300 in the same incision pattern. Moreover, incisions 250 can originate from the anterior side 460 and the posterior side 470 of the ophthalmic tissue 300 in an alternating manner. Additionally, incisions 250 can originate in the internal structure of a region of ophthalmic tissue 300 (e.g., between the anterior side 460 and posterior side 470) and extend through ophthalmic tissue 300 without breaking through either side 460, 470.

Alternating configurations of incisions 250 can be further shown in FIGS. 10-12. FIG. 10 shows a center line of incisions 250 originating from the posterior side 470 of the ophthalmic tissue 300 while outer lines of incisions 250 originate from the anterior side 460 of the ophthalmic tissue 300. FIG. 10 can illustrate the anterior side 460. The center line of incisions 250 originating from the posterior side 470 can be illustrated in phantom lines to indicate that the incisions 250 do not extend completely through the ophthalmic tissue 300. FIG. 11 shows the same configuration of incisions 250 in the ophthalmic tissue 300 under strain.

FIG. 12 illustrates a cross-sectional view of a set of alternating incisions 250 in ophthalmic tissue 300 under strain. Here, incisions 250 alternate between origination from the anterior side 460 and the posterior side 470 of a region of ophthalmic tissue 300. The depth 260, 270 of the incisions 250 can have a direct impact on the elastic properties of the ophthalmic tissue 300. In some cases, the alternating pattern of incisions 250 in ophthalmic tissue 300 can allow the tissue 300 to bend out in a transverse direction under strain, whereas other incision patterns can cause the tissue 300 to stretch along a single side 460, 470. This bending feature can allow more elongation of the ophthalmic tissue 300 under strain without compromising tissue strength by cutting too deeply into the tissue 300.

The bending feature can be illustrated by axes 430, 440, 450. The axes 430, 440, 450 can be normal to the layer of ophthalmic tissue 300. Referring to the example of FIG. 12, axes 430, 440, 450 can be traced on ophthalmic tissue 300 under strain where incisions 250 have been made. The axes 430, 440, 450 can be parallel when the ophthalmic tissue 300 contains no incisions 250. The axes 430, 440, 450 can extend obliquely or in a nonparallel manner with respect to one another when the ophthalmic tissue 300 is under strain and includes incisions 250.

The angles $\alpha$, $\beta$ between the axes 430, 440, 450 can increase as incision depth 260, 270 or strain increases. In particular, angle $\alpha$ can become larger as the depth 260 of the incision 250 directly below it increases. Angle $\alpha$ can also increase as a result of adjacent incisions 250 being made with greater depths 270 or greater strain being placed on the tissue 300. Similarly, angle $\beta$ can become larger as the depth 270 of the incision 250 directly above it increases and as a function of the depth 260 of adjacent incisions 250. The measure of the angles $\alpha$, $\beta$ can be related to the elasticity of the ophthalmic tissue 300 in the transverse direction. The angles $\alpha$, $\beta$ can measure between approximately 0 degrees and approximately 25 degrees, between approximately 5 degrees and approximately 15 degrees, or between approximately 10 and approximately 20 degrees, and/or other suitable values both larger and smaller.

Figure 13:
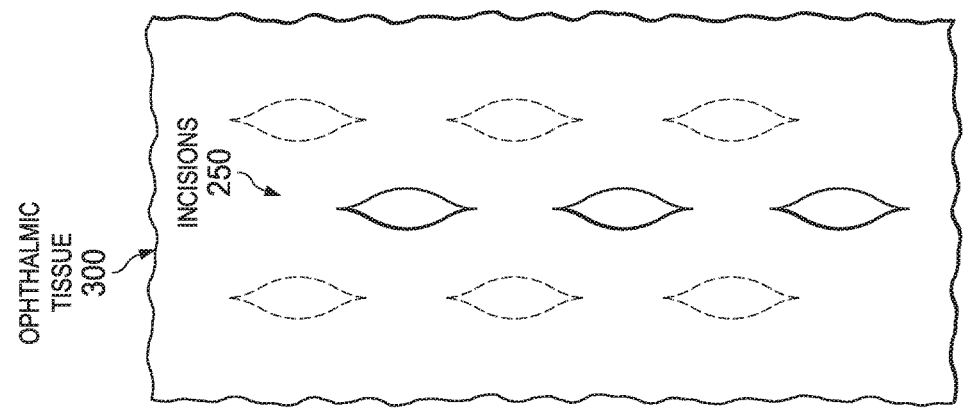
FIG. 13 illustrates a stressed region of ophthalmic tissue showing a set of incisions.

FIGS. 13-16 show several examples of incision patterns. In FIG. 13, a central line of incisions 250 can be made on the anterior side 460 of a layer of ophthalmic tissue 300 while outer lines of incisions 250 can be made on the posterior side 470.

Figure 14:
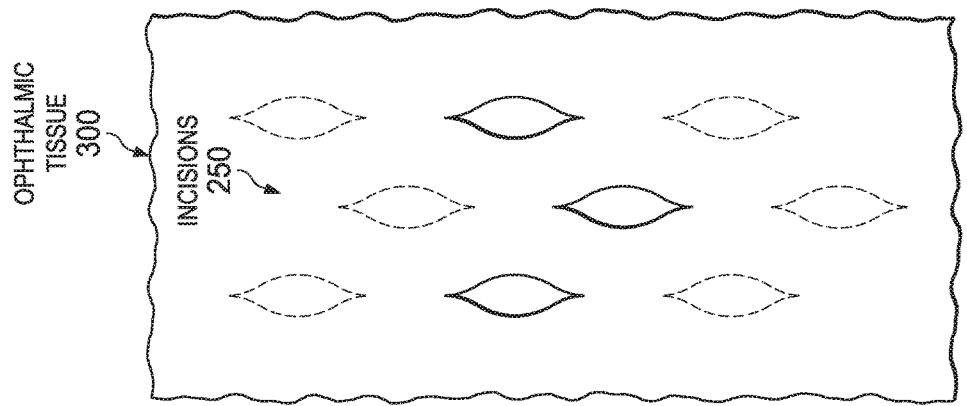
FIG. 14 illustrates a stressed region of ophthalmic tissue showing a set of incisions.

FIG. 14 illustrates a pattern of incisions 250 including three line segments. Each line segment can include incisions 250 originating in an alternating manner from the anterior side 460 and the posterior side 470 along the length of the ophthalmic tissue 300. The incisions 250 on the posterior side 470 can be grouped together, and the incisions 250 on the anterior side 460 can be grouped together.

Figure 15:
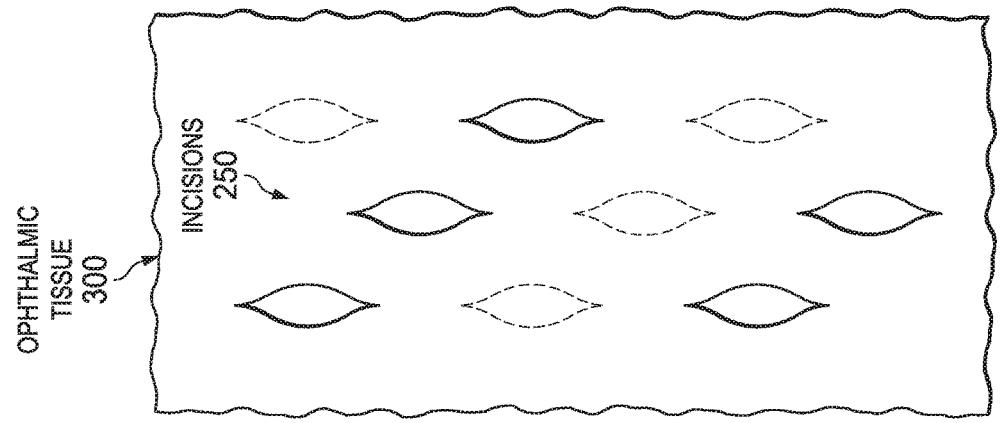
FIG. 15 illustrates a stressed region of ophthalmic tissue showing a set of incisions.

FIG. 15 illustrates another alternating pattern of incisions 250 in which diagonal lines of incisions 250 share a common origin on either the anterior side 460 or posterior side 470.

Figure 16:
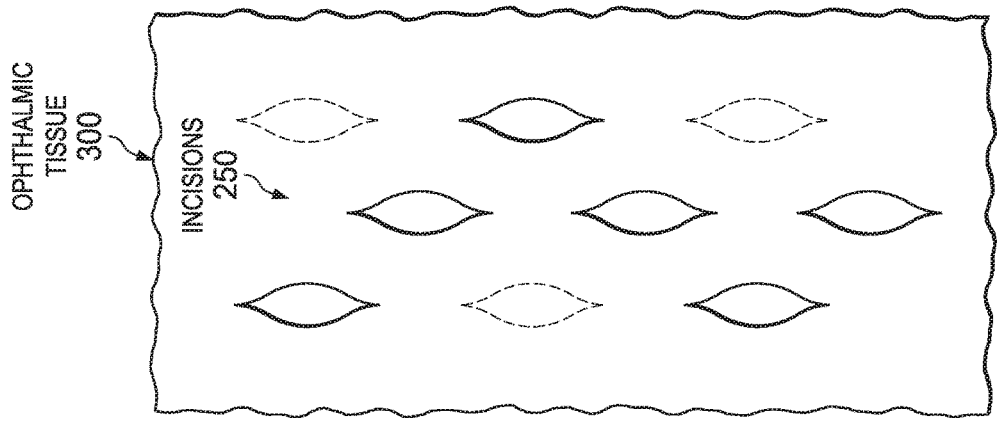
FIG. 16 illustrates a stressed region of ophthalmic tissue showing a set of incisions.

FIG. 16 illustrates a pattern of incisions 250 in which incisions 250 on the anterior side 460 can form a z-shaped pattern. The incisions 250 on the anterior side 460 can be bounded by the incisions 250 on the posterior side 470.

Figure 17:
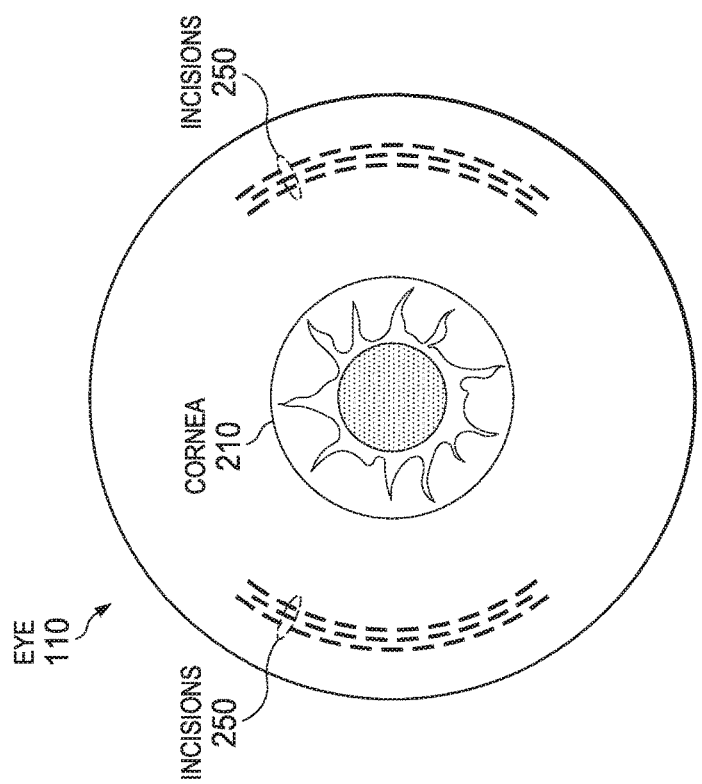
FIG. 17 illustrates a front view of an eye of a patient showing two sets of incisions.
Figure 18:
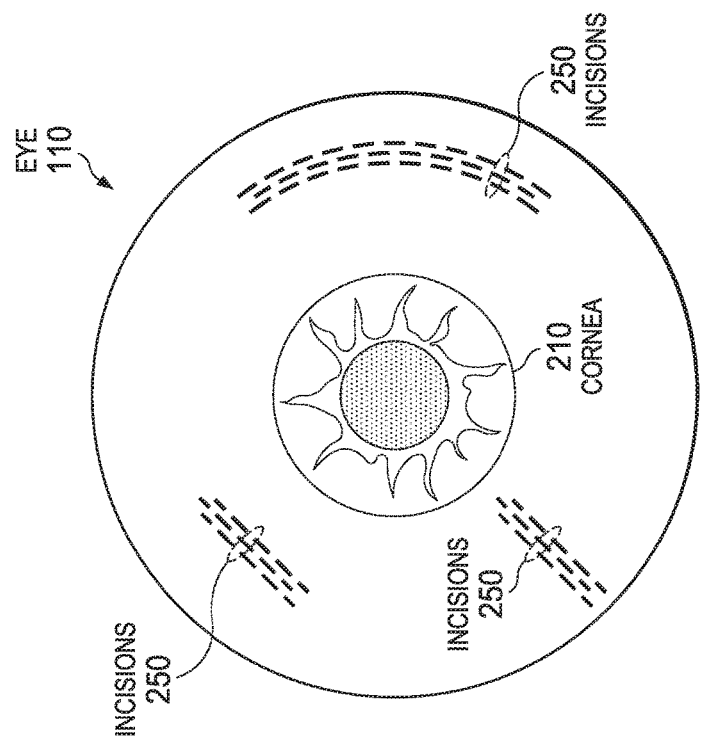
FIG. 18 illustrates a front view of an eye of a patient showing three sets of incisions.

FIGS. 17 and 18 show other exemplary incision patterns. FIG. 17 illustrates an incision pattern containing one or more arcs of incisions 250 disposed on one side of the cornea 210. A similar pattern can be disposed on the opposite side of the cornea 210. A third set or a fourth set of incisions 250 can be placed between the two sets shown in FIG. 17 around the circumference of the cornea 210.

FIG. 18 illustrates other incision patterns. On the right side of the eye 110, the incisions 250 can form one or more arcs. The one or more arcs can be concentrically positioned around the cornea 210. On the top left of the eye 110, the incisions 250 can be made in line segments disposed tangentially with respect to the cornea 210. On the bottom left of the eye 110, the incisions 250 can be disposed in line segments that extend radially from the cornea 210. All of the exemplary patterns shown in FIGS. 17 and 18 can include incisions 250 that originate on the anterior side 460 or posterior side 470 of the ophthalmic tissue 300, as discussed previously. The present disclosure can contemplate other orientations and shapes of line segments, including parallel lines, elliptical line segments, and polygonal patterns.

The number of incisions 250 forming a line segment as well as the number of separate line segments in a given incision pattern can vary. The number of incisions 250 that can form a line segment or arc within the incision pattern can include between 2 incisions and 20 incisions, between 2 incisions and 10 incisions, between 2 incisions and 6 incisions, and/or other suitable values both larger and smaller. A single line segment or arc can form an incision pattern, while in other cases, two, three, four, or five line segments or arcs can form an incision pattern. Combinations of the above lines and shapes can also be possible in a single incision pattern.

Figure 19:
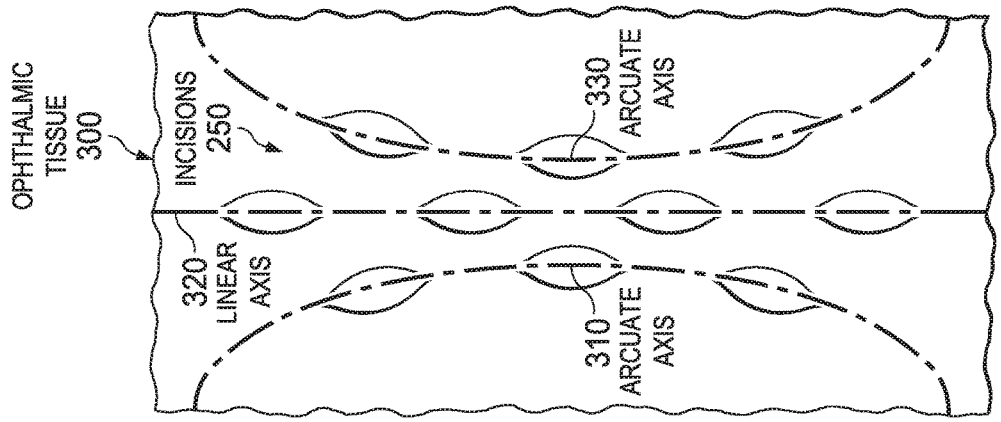
FIG. 19 illustrates a stressed region of ophthalmic tissue showing a set of incisions.

FIG. 19 shows another exemplary incision pattern. In this case, a central line of incisions 250 centered on linear axis 320 can be bounded by two arcuate lines with arcuate axes 310, 330. One of the arcuate lines can be disposed in a convex placement with respect to the cornea 210 while the other can be concentric or nearly concentric with respect to the cornea 210. Additionally, the axes 310, 330 of one or more of the outer lines can cross over the axis 320 of the inner line. The introduction of various arcuate lines can allow for more precise shaping of the cornea 210.

The present disclosure also includes methods of performing ophthalmic surgical procedures. For example, a laser beam 140 can be generated by means of a laser source 130. This beam 140 can be directed to an ocular target region. The laser beam 140 can be scanned along a scan pattern within the ocular target region to create a pattern of incisions for relaxing the ophthalmic tissue 300 in the ocular target region. In some cases, incisions 250 extend only partially through the ophthalmic tissue 300. As explained above, the pattern of incisions can include one or more sets of parallel lines, a cut mesh, a cut grating, or a pattern of staggered incisions, or a combination of these. Furthermore, the incisions 250 can originate from either the anterior side 460 or posterior side 470 of the ophthalmic tissue 300.

Embodiments as described herein can provide devices, systems, and methods of making incisions in ophthalmic tissue. The examples provided above can be exemplary in nature and not limiting. One skilled in the art may readily devise other systems consistent with the disclosed embodiments intended to be within the scope of this disclosure. As such, the application can be limited only by the following claims.

The invention claimed is:

1. A ophthalmic surgical laser system, comprising:
   a laser source, configured to generate a laser beam;
   a laser beam scanner, configured to
      direct the laser beam to an ocular target region; and
      scan the laser beam along a scan pattern in the ocular target region of an eye;
   instructions stored in a memory of a system controller in communication with the laser beam scanner, the instructions, when executed by the system controller, configured to cause the laser beam scanner to scan the laser beam along the scan pattern to create a pattern of cuts for relaxing ophthalmic tissue in the ocular target region, the ophthalmic tissue comprising a cornea of the eye, the cornea having an anterior side and a posterior side, wherein:

each cut of the pattern of cuts extends only partially through the ophthalmic tissue;

at least one cut of the pattern of cuts originates from the posterior side; and the pattern of cuts comprises a first segmented cut line and a second segmented cut line, the first segmented cut line comprising alternating cut and uncut segments staggered with respect to the alternating cut and uncut segments of the second segmented cut line.

2. The system of claim 1, wherein the pattern of cuts further comprises:

a third segmented cut line comprising alternating cut and uncut segments staggered with respect to at least one of the first segmented cut line and the second segmented cut line.

3. The system of claim 1, wherein:

the first segmented cut line comprises a first arc extending concentrically around the cornea of the eye; and the second segmented cut line comprises a second arc extending concentrically around the cornea of the eye.

4. The system of claim 3, wherein:

at least one cut of the first arc at least partially aligned with at least one cut of the second arc such that a ray originating from a center of the cornea passes through cuts of both the first arc and the second arc.

5. The system of claim 1, wherein:

the first segmented cut line and the second segmented cut line are parallel to each other.

6. The system of claim 1, wherein:

the first segmented cut line and the second segmented cut line extend at a different radius or angle relative to one another.

7. The system of claim 1, wherein:

the pattern of cuts creates a mesh structure of uncut ophthalmic tissue between a central portion and a peripheral portion of the ocular target region between two ends of the pattern of cuts.

8. The system of claim 1, wherein:

the ophthalmic tissue comprises a layer having an anterior side and a posterior side; and each of the cuts of the pattern of cuts extends through the ophthalmic tissue between about 10% and about 80% of a thickness between the anterior side and the posterior side of the ophthalmic tissue.

9. The system of claim 1, wherein the pattern of cuts comprises: cuts that originate from the anterior side and the posterior side of the ophthalmic tissue in an alternating manner.

10. The system of claim 1, wherein:

the pattern of cuts is configured to modify an elastic property of the region of ophthalmic tissue in a radial direction differently than in a tangential direction.

11. The system of claim 10, wherein:

the elastic property of the region of the ophthalmic tissue in the radial direction is increased more than the elastic property of the region of the ophthalmic tissue in the tangential direction by a factor of 2:1 or greater.

12. The system of claim 1, wherein:

the first segmented cut line comprises cuts on a first side of the cornea of the eye; and the second segmented cut line comprises cuts on a second side of the cornea, opposite the first side.

13. The system of claim 12, wherein the pattern of cuts further comprises:

a third segmented cut line positioned between the first side and the second side around a circumference of the cornea.

14. The system of claim 1, wherein the pattern of cuts comprises:

one or more lines that extend radially outward from the cornea of the eye.

15. A method of performing an ophthalmic surgical procedure, comprising the steps:

generating a laser beam with a laser source;

directing the laser beam to an ocular target region;

scanning the laser beam along a scan pattern within the ocular target region to create a pattern of cuts for relaxing ophthalmic tissue in the ocular target region, the ophthalmic tissue comprising a cornea of the eye, the cornea having an anterior side and a posterior side, wherein:

each cut of the pattern of cuts extends only partially through the ophthalmic tissue;

at least one cut of the pattern of cuts originates from the posterior side; and the pattern of cuts comprises a first segmented cut line and a second segmented cut line, the first segmented cut line comprising alternating cut and uncut segments staggered with respect to the alternating cut and uncut segments of the second segmented cut line.

16. The method of claim 15, wherein the pattern of cuts further comprises:

a third segmented cut line comprising alternating cut and uncut segments staggered with respect to at least one of the first segmented cut line and the second segmented cut line.

17. The method of claim 15, wherein the first segmented cut line comprises a first arc extending concentrically around the cornea of the eye; and the second segmented cut line comprises a second arc extending concentrically around the cornea of the eye.

18. The method of claim 15, wherein the pattern of cuts modifies an elasticity of the region of ophthalmic tissue in a radial direction differently than in a tangential direction.

19. The method of claim 18, wherein:

the elasticity of the region of the ophthalmic tissue in the radial direction is increased more than the elasticity of the region of the ophthalmic tissue in the tangential direction by a factor of 2:1 or greater.

* * * * *